(12) United States Patent
Vitello et al.

(10) Patent No.: US 11,413,406 B1
(45) Date of Patent: Aug. 16, 2022

(54) TAMPER EVIDENT ASSEMBLY

(71) Applicants: Jonathan J. Vitello, Ft. Lauderdale, FL (US); Timothy Brandon Hunt, Hollywood, FL (US); Robert Banik, Hollywood, FL (US)

(72) Inventors: Jonathan J. Vitello, Ft. Lauderdale, FL (US); Timothy Brandon Hunt, Hollywood, FL (US); Robert Banik, Hollywood, FL (US)

( * ) Notice: Subject to any disclaimer, the term of this patent is extended or adjusted under 35 U.S.C. 154(b) by 149 days.

(21) Appl. No.: 16/599,918

(22) Filed: Oct. 11, 2019

Related U.S. Application Data

(63) Continuation-in-part of application No. 15/912,300, filed on Mar. 5, 2018, now Pat. No. 10,758,684.

(60) Provisional application No. 62/744,523, filed on Oct. 11, 2018.

(51) Int. Cl.
*A61M 5/50* (2006.01)

(52) U.S. Cl.
CPC .................. *A61M 5/5086* (2013.01)

(58) Field of Classification Search
CPC .............. A61M 5/5086; A61M 5/3134; A61M 5/3135; A61M 2205/276
See application file for complete search history.

(56) References Cited

U.S. PATENT DOCUMENTS

| | | | |
|---|---|---|---|
| 722,943 A | 3/1903 | Chappell | |
| 732,662 A | 6/1903 | Smith | |
| 1,678,991 A | 7/1928 | Marschalek | |
| 1,970,631 A | 8/1934 | Sherman | |
| 2,477,598 A | 8/1949 | Hain | |
| 2,739,590 A | 3/1956 | Yochem | |
| 2,823,674 A | 2/1958 | Yochem | |
| 2,834,346 A | 5/1958 | Adams | |
| 2,875,761 A | 3/1959 | Helmer et al. | |
| 2,888,015 A | 5/1959 | Hunt | |
| 2,952,255 A | 9/1960 | Hein, Jr. | |
| 3,122,280 A | 2/1964 | Goda | |
| 3,245,567 A | 4/1966 | Knight | |
| 3,323,798 A | 6/1967 | Miller | |
| 3,364,890 A | 1/1968 | Andersen | |

(Continued)

FOREIGN PATENT DOCUMENTS

| EP | 0148116 A | 7/1985 |
|---|---|---|
| GB | 486367 | 6/1938 |

(Continued)

*Primary Examiner* — Amber R Stiles
(74) *Attorney, Agent, or Firm* — Malloy & Malloy, PL; Jennie S. Malloy; Peter A. Matos

(57) ABSTRACT

A tamper evident assembly for retaining a plunger and/or piston within a barrel of a syringe comprises an elongated tether disposed in an operative attachment and position on the syringe. When operatively attached, a connector assembly adjustably and fixedly interconnects the tether to an exterior of the barrel of the syringe concurrently to one end of the tether, and with a retaining member associated with the opposite end of the tether disposed in a removal restrictive relation to the plunger and/or piston, on the interior of the barrel. Movable adjustment of the tether relative to the connector assembly defines a retaining segment which can be disposed into a fixed length and taut orientation, between the ends of the tether, to further define the operative attachment or position.

18 Claims, 12 Drawing Sheets

(56) References Cited

U.S. PATENT DOCUMENTS

| | | |
|---|---|---|
| 3,368,673 A | 2/1968 | Johnson |
| 3,574,306 A | 4/1971 | Alden |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,726,445 A | 4/1973 | Ostrowsky et al. |
| 3,747,751 A | 7/1973 | Miller et al. |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 3,987,930 A | 10/1976 | Fuson |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| 4,482,071 A | 11/1984 | Ishiwatari |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,742,910 A | 5/1988 | Staebler |
| 4,743,229 A | 5/1988 | Chu |
| 4,743,231 A | 5/1988 | Kay et al. |
| 4,760,847 A | 8/1988 | Vaillancourt |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,024,323 A | 6/1991 | Bolton |
| 5,049,129 A | 9/1991 | Zdeb et al. |
| 5,057,093 A | 10/1991 | Clegg et al. |
| D323,392 S | 1/1992 | Byrne |
| 5,085,332 A | 2/1992 | Gettig et al. |
| 5,090,564 A | 2/1992 | Chimienti |
| 5,135,496 A | 8/1992 | Vetter et al. |
| 5,163,922 A | 11/1992 | McElveen, Jr. et al. |
| 5,165,560 A | 11/1992 | Enniss, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,370,226 A | 12/1994 | Gollobin et al. |
| 5,380,295 A | 1/1995 | Vacca |
| 5,402,887 A | 4/1995 | Shillington |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,957,314 A | 9/1999 | Nishida et al. |
| 5,989,227 A | 11/1999 | Vetter et al. |
| 5,993,437 A | 11/1999 | Raoz |
| 6,000,548 A | 12/1999 | Tsais |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,279,746 B1 | 4/2001 | Hussaini et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,358,241 B1 | 3/2002 | Shapeton et al. |
| 6,375,640 B1 | 4/2002 | Teraoka |
| 6,394,983 B1 | 5/2002 | Mayoral et al. |
| 6,439,276 B1 | 8/2002 | Wood et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanley et al. |
| 6,755,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,942,643 B2 | 9/2005 | Eakins et al. |
| 7,036,661 B2 | 5/2006 | Anthony et al. |
| 7,055,273 B2 | 6/2006 | Roshkoff |
| 7,125,397 B2 | 10/2006 | Woehr et al. |
| 7,141,286 B1 | 11/2006 | Kessler et al. |
| 7,182,256 B2 | 2/2007 | Andreasson et al. |
| 7,240,926 B2 | 7/2007 | Dalle et al. |
| 7,374,555 B2 | 5/2008 | Heinz et al. |
| 7,404,500 B2 | 7/2008 | Marteau et al. |

(56) References Cited

U.S. PATENT DOCUMENTS

| | | |
|---|---|---|
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,497,330 B2 | 3/2009 | Anthony et al. |
| 7,503,453 B2 | 3/2009 | Cronin et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,413,811 B1 | 4/2013 | Arendt |
| 8,443,999 B1 | 5/2013 | Reinders |
| D684,057 S | 6/2013 | Kwon |
| 8,512,277 B2 | 8/2013 | Del Vecchio |
| 8,528,757 B2 | 9/2013 | Bisio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,016,473 B2 | 4/2015 | Tamarindo |
| 9,101,534 B2 | 8/2015 | Bochenko |
| D738,495 S | 9/2015 | Strong et al. |
| 9,125,976 B2 | 9/2015 | Uber, III et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| D750,228 S | 2/2016 | Strong et al. |
| 9,272,099 B2 | 3/2016 | Limaye et al. |
| 9,311,592 B1 | 4/2016 | Vitello et al. |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 1/2017 | Schultz |
| 9,662,456 B2 | 5/2017 | Woehr |
| D789,529 S | 6/2017 | Davis et al. |
| 9,687,249 B2 | 6/2017 | Hanlon et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello et al. |
| D815,945 S | 4/2018 | Fischer |
| D820,187 S | 6/2018 | Parker |
| 9,987,438 B2 | 6/2018 | Stillson |
| D825,746 S | 8/2018 | Davis et al. |
| 10,039,913 B2 | 8/2018 | Yeh |
| D831,201 S | 10/2018 | Holtz et al. |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,315,808 B2 | 6/2019 | Taylor et al. |
| 10,376,655 B2 | 8/2019 | Pupke et al. |
| D859,125 S | 9/2019 | Weagle et al. |
| 10,758,684 B1 | 9/2020 | Vitello et al. |
| 10,773,067 B2 | 9/2020 | Davis et al. |
| 10,898,659 B1 | 1/2021 | Vitello et al. |
| 10,912,898 B1 | 2/2021 | Vitello et al. |
| 10,933,202 B1 | 3/2021 | Banik |
| 10,953,162 B1 | 3/2021 | Hunt et al. |
| 11,040,149 B1 | 6/2021 | Banik |
| 11,040,154 B1 | 6/2021 | Vitello et al. |
| 11,097,071 B1 | 8/2021 | Hunt et al. |
| 11,278,681 B1 | 3/2022 | Banik et al. |
| D948,713 S | 4/2022 | Banik |
| 2001/0003150 A1 | 6/2001 | Imbert |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0046962 A1 | 4/2002 | Vallans et al. |
| 2002/0097396 A1 | 7/2002 | Schafer |
| 2002/0099334 A1 | 7/2002 | Hanson et al. |
| 2002/0101656 A1 | 8/2002 | Blumenthal et al. |
| 2002/0104770 A1 | 8/2002 | Shapeton et al. |
| 2002/0133119 A1 | 9/2002 | Eakins et al. |
| 2003/0146617 A1 | 8/2003 | Franko, Sr. |
| 2003/0183547 A1 | 10/2003 | Heyman |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0303267 A1 | 12/2008 | Schnell et al. |
| 2008/0306443 A1 | 12/2008 | Neer |

(56) References Cited

U.S. PATENT DOCUMENTS

| | | |
|---|---|---|
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0166311 A1 | 7/2009 | Claessens |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1* | 2/2011 | Felsovalyi ......... A61M 5/31511 604/218 |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin |
| 2014/0353196 A1 | 12/2014 | Key |
| 2015/0182686 A1 | 7/2015 | Okihara |
| 2015/0191633 A1 | 7/2015 | De Boer et al. |
| 2015/0302232 A1 | 10/2015 | Strassburger et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0250420 A1 | 9/2016 | Maritan et al. |
| 2016/0279032 A1 | 9/2016 | Davis |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0225843 A1 | 8/2017 | Glaser et al. |
| 2017/0239141 A1 | 8/2017 | Davis et al. |
| 2017/0319438 A1 | 11/2017 | Davis et al. |
| 2017/0354792 A1 | 12/2017 | Ward |
| 2018/0001540 A1 | 1/2018 | Byun |
| 2018/0014998 A1 | 1/2018 | Yuki et al. |
| 2018/0078684 A1 | 3/2018 | Peng et al. |
| 2018/0089593 A1 | 3/2018 | Patel et al. |
| 2018/0098915 A1 | 4/2018 | Rajagopal et al. |

FOREIGN PATENT DOCUMENTS

| | | |
|---|---|---|
| WO | WO2008/000279 | 1/2008 |
| WO | WO 2017086607 | 5/2015 |

* cited by examiner

TAMPER EVIDENT ASSEMBLY

CLAIM OF PRIORITY

The present application is a Continuation-In-Part (CIP) application of and claims priority to a previously filed, U.S. Non-Provisional patent application, namely, that having Ser. No. 15/912,300 and a filing date of Mar. 5, 2018, which has matured into Patent No. 10,758,684 on Sep. 1, 2020, and further, claims priority to a previously filed, U.S. Provisional patent application, namely, that having Ser. No. 62/744,523 and a filing date of Oct. 11, 2018, with the contents of both prior applications being incorporated herein by reference in their entireties.

BACKGROUND OF THE INVENTION

Field of the Invention

This invention is directed to a tamper evident assembly structured to restrict access to a drug or other contents in a loaded syringe by preventing removal of the syringe plunger and/or piston from the interior of the syringe barrel, through the open end thereof. Disconnection of the tamper evident assembly from an intended "removal preventing relation" to the piston is at least one indication of tampering with or use of the syringe.

Description of the Related Art

In the medical field, it is a relatively common for authorized medical personnel to prescribe a drug or medication for a patient which is to be given by injection or other procedures, such as the administration of fluids to the patient by intravenous (IV) infusion. It is also a relatively common procedure for syringes and other drug administering devices to be pre-loaded or filled by a pharmacist or other authorized personnel, whether within the hospital or at another facility and/or location, at what may be generally referred to as a filling station. However, a filling station is typically located in a remote part of the hospital or other facility, relative to the patient care area where the injection is to be administered. Indeed, at large medical facilities, a filling station may resemble a factory on the hospital grounds from which drugs and other fluids are delivered to multiple nursing stations at different locations. Because of the remote location of many nurse's stations relative to a filling station, a fluid or drug loaded administering device is very often given to another person for delivery to a nurse's station for subsequent dosing of the patient by a duly qualified nurse or other medically trained person. As a result, a pre-loaded syringe may travel quite some distance and be handled by several people before it reaches a nurse's station, which raises some concern that the contents of the syringe may be tampered with or which might otherwise cause the sterility of the syringe and/or its contents to be compromised.

Additionally, in the case where a drug has been prescribed that is a very expensive or addictive, such as but not limited to morphine, and has been pre-loaded in the syringe or other administering device, there is a heightened danger that the pre-loaded syringe or other administering device will be tampered with at some point, by a person seeking unauthorized access to the drug. This possibility can present a real danger if such a person were to gain access to the prescribed medicine and then, inappropriately and without concern, substitute some other, unauthorized material in the syringe which looks like the actual prescribed medicine and dosage. By way of an example only, if saline solution or water or another drug were substituted for a dose of morphine, the patient would not receive the prescribed drug which by itself, could be quite harmful, while the substituted content might potentially also cause the patient serious harm. Thus, there is a problem of knowing if a sealed, pre-loaded syringe or other administering device has, or has not, been exposed to contamination or might otherwise have been compromised by its being tampered with. This and related types of problems have been described in one or more previously issued U.S. patents, such as U.S. Pat. No. 5,328,474.

Therefore, to overcome the disadvantages and problems of utilizing a pre-filled syringe, it is desirable, if not necessary, to utilize a "tamper evident structure" to prevent, or at least restrict, access to a prescribed medication or other contents of a pre-filled syringe. If, in fact, access by an unauthorized person has been accomplished or even attempted to a pre-filled syringe or other drug administering device, the goal of such tamper evident structures is to provide a clear indication of having been tampered with.

By way of an example, one method of accessing, without authorization, the contents of a pre-filled syringe involves a removal of the syringe's plunger from the interior of the barrel of the syringe, through the open end thereof. As this is an alternative and somewhat unexpected way of accessing drugs and medication without authorization, there is a need in the medical field and in the area of tamper evident structures to protect a syringe that is pre-filled or otherwise filled with a prescribed medication or other contents, so as to restrict or prevent access to the contents thereof, or in the alternative, to provide a clear visual indication that tampering with the syringe has occurred or that use of the syringe, such as by a nurse or other authorized personnel, has been accomplished.

SUMMARY OF THE INVENTION

The present invention is intended to present a solution to these and other needs that remain in this field of art, and as such, is directed to a tamper evident assembly for preventing or at least restricting access to the interior of a syringe, and more specifically, to the medicine or other contents of a loaded syringe. In accomplishing such restrictive access, the tamper evident assembly of the present invention is operatively disposed and structured to restrict the removal of a plunger from the interior of the barrel of the syringe.

As will become clear from the description of the invention below, one or more of the components of the tamper evident assembly operate either individually or in combination to provide a clear indication of "tampering" with the syringe, if an unauthorized attempt to access the contents of the pre-filled syringe has been attempted. Similarly, authorized use of the syringe will also be clearly evident.

Accordingly, the tamper evident assembly of the present invention is specifically, but not exclusively, adapted for use with a syringe loaded with a medicine, typically but not limited to a "pre-filled syringe" such as described above and commonly used in the medical profession. The preventing or restricting the removal of the syringe's plunger, including in most embodiments the piston or stopper thereof will restrict access to the drug or medicinal contents of the loaded or pre-filled syringe through the open end of the syringe barrel, which might otherwise occur if the plunger or piston were not present.

In more specific terms, the tamper evident assembly comprises an elongated tether having a proximal end and a distal end oppositely disposed to one another. The tamper evident assembly further includes a cover structured to be disposed in enclosing, covering relation to a discharge port or nozzle through which the drug or medicinal contents of a pre-filled syringe is normally dispensed and given to a patient. The cover may also include a tamper evident structure such as, but not limited to, a closure disposed in flow restricting relation to the nozzle or discharge port of the syringe. In addition to the structuring of the elongated tether, and in order to enhance the tamper evident capabilities of the inventive assembly, the cover may include any one of a number of "tamper evident closures" or "caps".

The assembly of the present invention further includes a connector assembly adjustably and fixedly connecting the elongated tether to the cover, so as to assume an operative position. In at least one embodiment, the connector assembly is connected directly to or in direct association and/or adjacent relation to the cover, so as to establish and maintain both the tether and the cover concurrently in a position which prevents or restricts removal of the stopper or piston on the plunger of the syringe from the open end of the syringe barrel. Further, the tamper evident assembly of the present invention includes cooperative structuring between the connector assembly and at least the distal end of the elongated tether, so as to establish a one-way drive or passage of the distal end through the connector assembly. Such a one-way passage or direction of travel facilitates a stable, fixed connection between the cover and the distal end of the tether, and may be accomplished by a ratchet connector or other appropriate structure.

The operative position is further defined by the proximal end of the tether being connected to the barrel of the syringe, preferably at an opposite end thereof, so as to be disposed in a "removal preventing relation" with the plunger of the syringe, and preferably, the stopper or piston thereof. As such, the proximal end of the tether is at least partially disposed within a portion of the hollow interior of the syringe barrel such as, but not limited to, through the open end of the barrel. This may be effectively accomplished by defining an extremity of the tether's proximal end, and or other appropriate portion of tether and/or proximal end, to have a small "hook" like structure, capable of extending over the perimeter of the open end of the syringe barrel and into the aforementioned "removal preventative relation" to the syringe plunger. As a result, when the proximal end of the tether is disposed at least partially within the interior of the syringe barrel, it is further disposed to interrupt movement of the piston by engagement therewith, prior to the piston reaching the open end of the barrel. Access to the interior of the syringe barrel and the medicine or other contents therein will thereby be prevented, due to an inability to remove the piston or stopper through the barrel's open end.

Therefore, an attempt to remove the piston or stopper of the plunger from the interior of the barrel is prevented or at least restricted by the disposition of both the tether and the cover in a fixed connection to one another. Moreover, such a fixed connection is accomplished while the cover is disposed in covering, enclosing and/or flow restricting relation to the nozzle or discharge port of the syringe, concurrent to the proximal end of the tether being disposed at least partially within the interior of the barrel, in the aforementioned removal preventative relation to the piston.

Other structural and operative features of the tamper evident assembly include the provision of a "retaining segment" defined by a length of the tether extending between its proximal end, disposed near or at the open end of the syringe barrel in the operative position, and the cover connected to the discharge port or nozzle at the opposite end of the syringe. Further, when the tamper evident assembly is disposed in the completed, assembled operative position, the retaining segment has a taut, fixed length, orientation and is disposed on the exterior of the barrel. The establishment and maintenance of the retaining segment in the taut, fixed length, orientation is facilitated by the distal end of the tether being cooperatively structured with the connector assembly so as to only move through the connector assembly in a single direction. Also, once the taut, fixed length of the retaining segment has been established, the distal end of the tether may be "locked" in place relative to the connector assembly. Therefore, the taut, fixed length orientation of the retaining segment is defined and maintained by the distal end of the tether and the connector assembly being cooperatively structured to define a length adjusting, one-way movement of said distal end through or in movable engagement with the connector assembly and relative to the cover.

As a result, when the retaining segment is so oriented, both the proximal end of the tether and the cover will be fixedly interconnected to one another and also, be respectively connected in fixed relation to the open end of the syringe barrel and also to the fitting and/or nozzle/discharge port of the syringe. Therefore, access to the drug or other contents on the interior of the syringe barrel through the open end, as well as the discharge port of the syringe, will be prevented or significantly restricted. If a person should tamper with a loaded syringe having the inventive assembly deployed thereon or try to access a drug or medicine carried within it, the inventive assembly described herein will provide an indication of tampering or use. Such indication will be in the form of breakage, damage, removal, etc. of the tether and/or cover.

In order to further enhance the tamper evident capabilities, in at least one embodiment the tether may include at least one frangible link or structure integrally formed along its length between the proximal and distal ends thereof. The integrity or like structural features of the frangible link may be such as to cause a breakage thereof when forces are exerted on the tether as a result of an attempt to remove or rearrange the tether and/or the cover.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
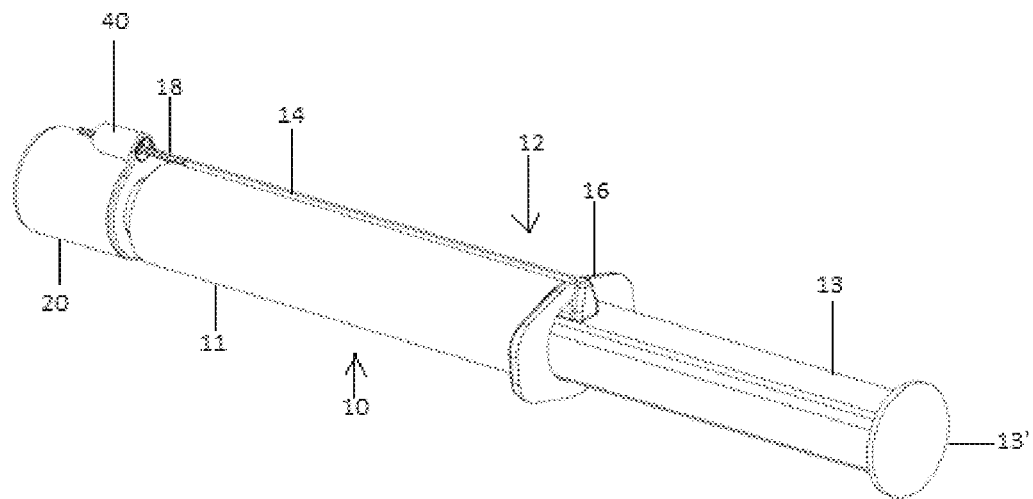
FIG. 1 is a perspective view of a tamper evident assembly according to the present invention illustrated as being connected and in an assembled, operative position relative to a syringe.
Figure 7:
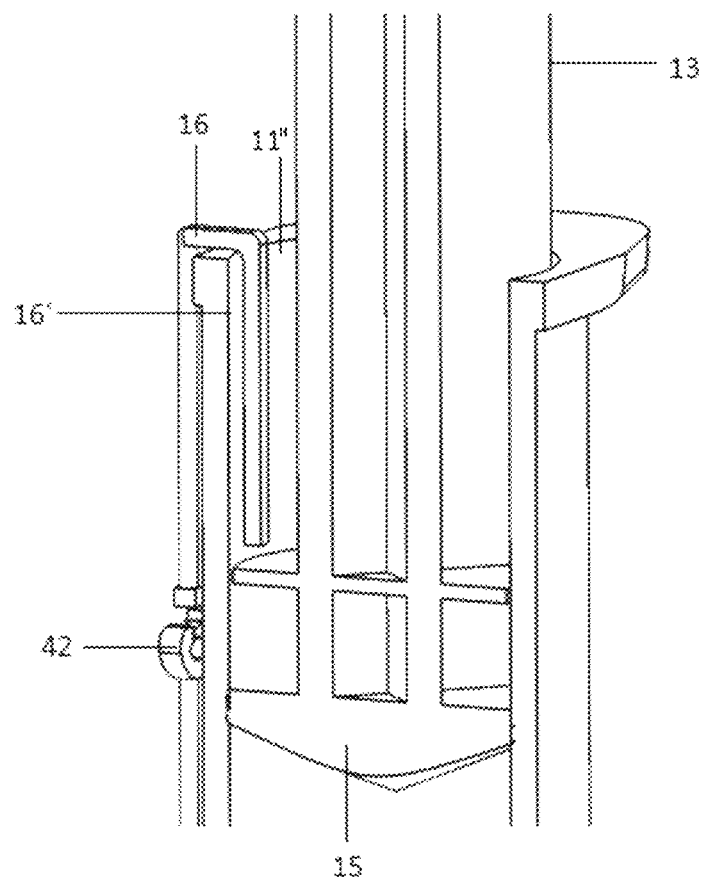
FIG. 7 is a perspective view in partial cutaway of the at least one frangible member of the embodiment of FIGS. 5 and 6 in a connected orientation.
Figure 7A:
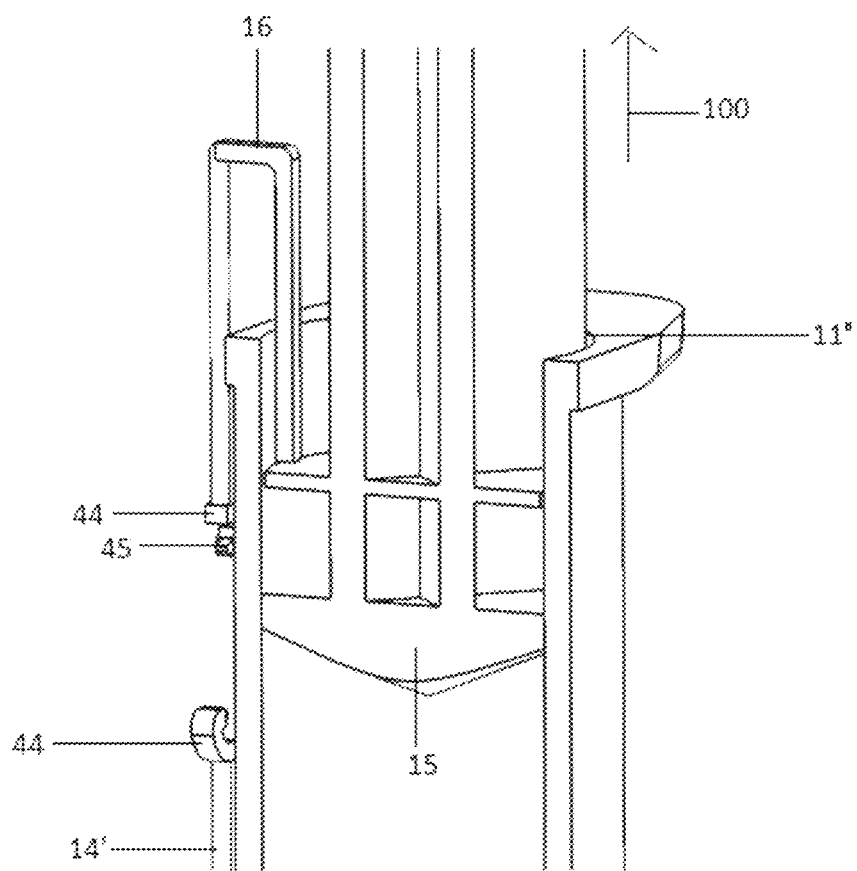
FIG. 7A is a perspective view in partial cutaway of the at least one frangible member of the embodiment of FIGS. 5, 6 and 7 in a broken or disconnected orientation.

As represented throughout the Figures, the present invention is directed to an assembly, structured to have tamper evident capabilities, which prevents or restricts access to the interior of a syringe, generally indicated as 10 such as, but not limited to, a syringe that has been filled with a drug, medicine or other content. In the illustrated embodiment of FIG. 1, the tamper evident assembly 12 of the present invention is represented in an assembled and operative position. Further, when in this assembled and operative position, the tamper evident assembly 12 is disposed in cooperative connection, attachment or otherwise in direct association with the syringe 10 of the type including a barrel 11 and a hollow interior 11' (shown in FIG. 4) in which a drug, medicine or other contents may be filled and stored for a period of time. Also, and as perhaps best shown in FIGS. 7 and 7A, the syringe 10 includes an open end 11" through which a plunger 13 enters the hollow interior 11' of the barrel 11. As shown in FIG. 1, the plunger 13 also includes a terminal end 13' at one end, and as shown in FIGS. 7 and 7A, a piston or stopper 15 connected to the opposite end thereof.

Figure 2:
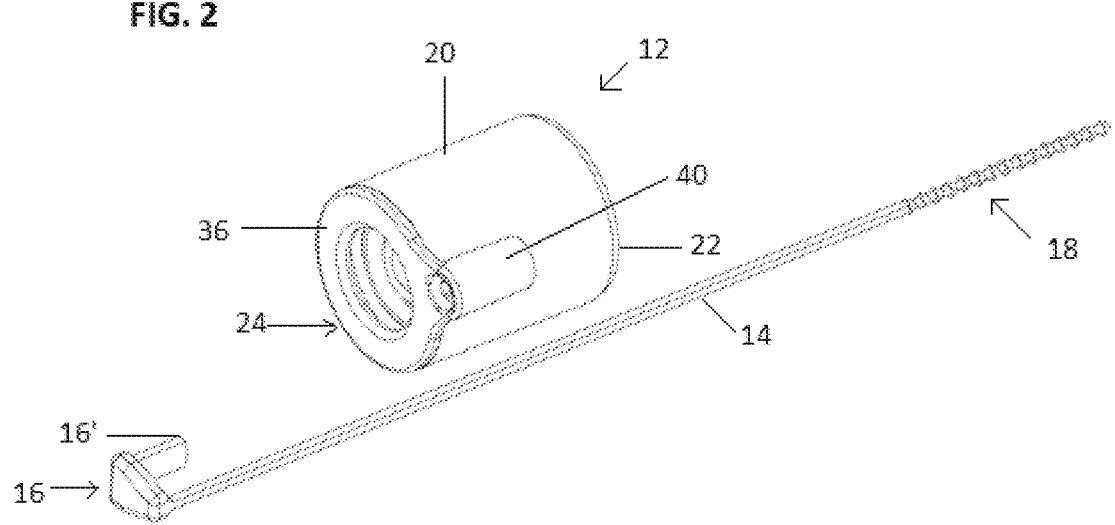
FIG. 2 is an exploded view of an elongated tether, cover and connector assembly in an unassembled state, representing at least some of the operative components of a tamper evident assembly according to the present invention, such as the embodiment shown in FIG. 1, but in a reverse orientation to the assembled components shown therein.
Figure 8:
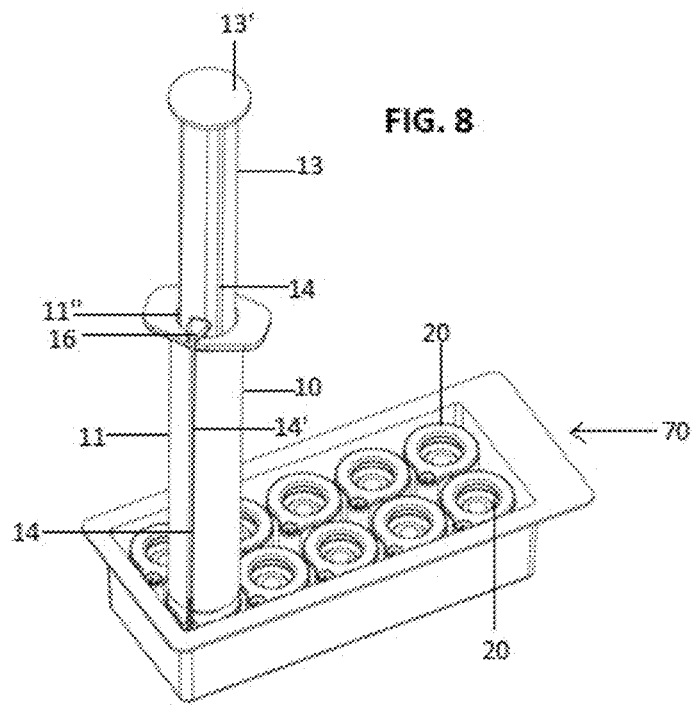
FIG. 8 is a perspective view of a container for packaging one or more covers in the form of tamper evident closures for the inventive tamper evident assembly described herein and shown in the embodiments of FIGS. 1-5, and a connecting orientation of a syringe with a selected one of such closures.
Figure 9:
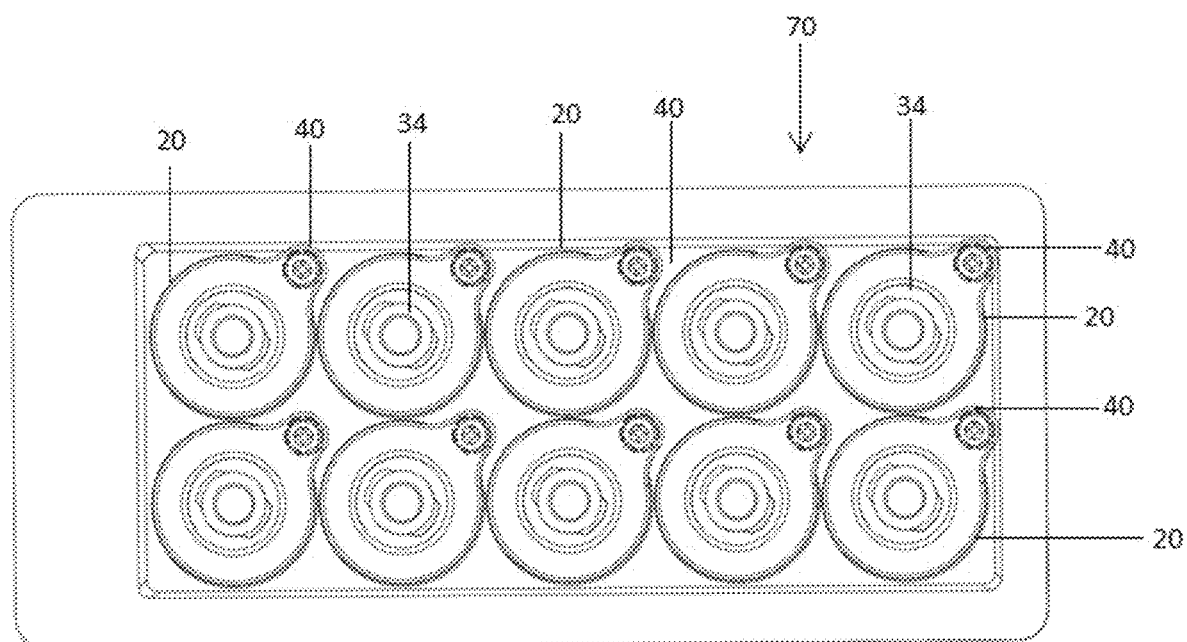
FIG. 9 is a top plan, interior view of the container and a plurality of covers in the form of tamper evident closures contained therein, as represented in FIG. 8.

With reference now to FIG. 2, the tamper evident assembly 12 according to the present invention is represented in an unassembled state and includes an elongated tether 14 having a proximal end 16 and a distal end 18. Further, the tamper evident assembly 12 includes a cover 20 having a closed end 22 and an open or access end 24. It is emphasized that the cover 20 may assume a variety of different structural configurations and operative capabilities, and may further be structured to include any one of a plurality of different tamper evident closures, as shown in FIGS. 8 and 9.

Figure 4:
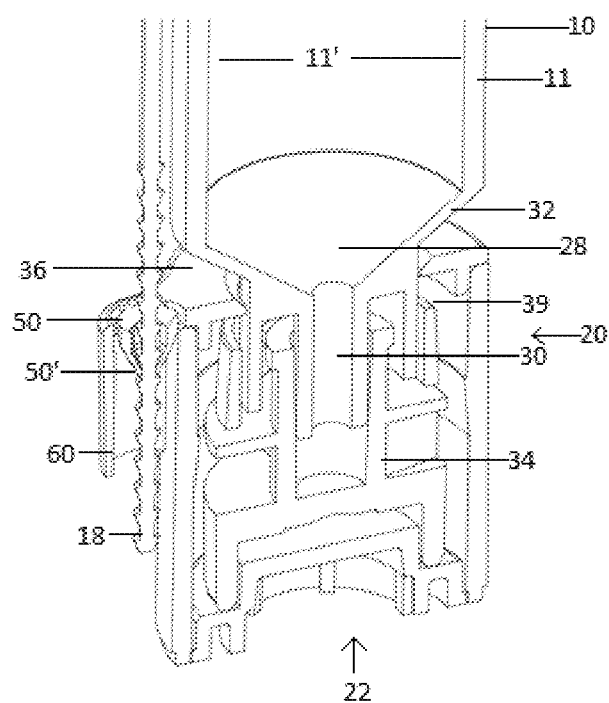
FIG. 4 is a perspective, interior sectional view in partial cutaway representing a cover of the tamper evident assembly of the present invention secured to a syringe.

By way of example, and as represented in FIG. 4, the cover 20 is structured to engage and at least partially enclose the nozzle or discharge port of a syringe 10, such as at what may be referred to as a "fitting" 28 of the syringe 10. As used herein the term "fitting" is meant to include the discharge end 32 of the syringe 10, including a nozzle and/or discharge port 30 integrally formed with or otherwise fixedly connected or associated with the discharge end 32. As set forth above, the cover 20 may be in the form of a tamper evident closure such as is shown in FIGS. 8 and 9, and may include a tip cap, generally indicated as 34, disposed in flow restricting relation to the syringe fitting 28, and more specifically, to the syringe nozzle or discharge port 30, as perhaps best shown in FIG. 4. It is again emphasized, however, that any one of a plurality of different covers 20, may be incorporated in the tamper evident assembly 12, wherein the different covers may or may not be tamper evident closures or otherwise include tamper evident capabilities. It should be further evident that the cover 20 is appropriately structured to be connected or attached to the fitting 28 and/or discharge port 30 of a syringe 10 in a manner which prevents access to the contents of the interior chamber 11' of the syringe barrel 11, through the fitting 28 and/or discharge port 30.

With reference again to FIG. 2, as an additional precaution for preventing access to the fitting 28 of the syringe 11 and/or for trying to defeat the protective structural features of the cover 20, the cover 20 may include a collar 36. The collar 36 is fixedly or removably connected adjacent to the access end or open and 24 of the cover 20. In such a location, the collar 26 effectively closes the spaces or open areas 39, as represented in FIG. 4. Absent the collar 36 or other equivalent structure, the openings or spaces 39 may be sufficiently large to allow for the access of a tool, such as a paperclip, screw driver or other instrument, into the interior of the cover 20 to defeat its protective features or structural components.

With further reference to FIG. 2, and as set forth above, the tamper evident assembly 12 of the present invention includes an elongated tether 14. The tether 14 may be formed of an at least partially flexible and/or semi-rigid material, or potentially of other materials having an increased structural integrity or rigidity. In certain instances, the tether 14 may be less than semi-rigid and more flexible, and even initially loosely oriented until disposed in the completed and assembled operative position represented in at least FIGS. 1 and 5. When in the completed and/or assembled operative position, the proximal end 16 of the elongated tether 14 is connected to the barrel of the syringe, preferably at and/or partially through the open end 11" thereof. As also shown in FIG. 2, the proximal end 16 of the tether 14 preferably includes an outwardly extending, depending member 16', which may be at least generally shaped to define a "hook" like configuration. Accordingly, when in its operative position, the proximal end 16 and/or hook like structure 16' is sized and configured to extend in overlying relation to the perimeter of syringe barrel 11 at open end 11" as best shown in FIGS. 1 and 8. When so disposed, the hook like depending member 16' is disposed on the hollow interior chamber 11' of the syringe barrel 11, generally adjacent the open end 11" thereof and between the open end 11" and the stopper or piston 15, with the latter being perhaps best illustrated in FIGS. 7 and 7A. In such a position, the proximal end 16 of the tether, and the hook like depending member 16' thereof, are disposed in a "removal preventing relation" to the piston or stopper 15 at one end of the plunger 13 of the syringe.

Therefore, removal of the plunger 13 of the syringe 10, and in particular, of the piston or stopper 15, from the interior chamber 11' of the syringe barrel 11, through its open end 11", is prevented or at least restricted by the concurrent disposition of both the tether 14 and the cover 20 in fixedly connected relation to one another. The completed and/or assembled operative position is thereby defined. Moreover, such a fixed connection is accomplished by the cover 20 being disposed in covering, enclosing and/or flow restricting relation to the fitting 28 and/or discharge port 30 of the syringe 10, concurrent to the proximal end 16 of the tether 14 being disposed at least partially within the interior 11" of the barrel 11, in the aforementioned "removal preventing relation" to the piston or stopper 15.

Figure 3:
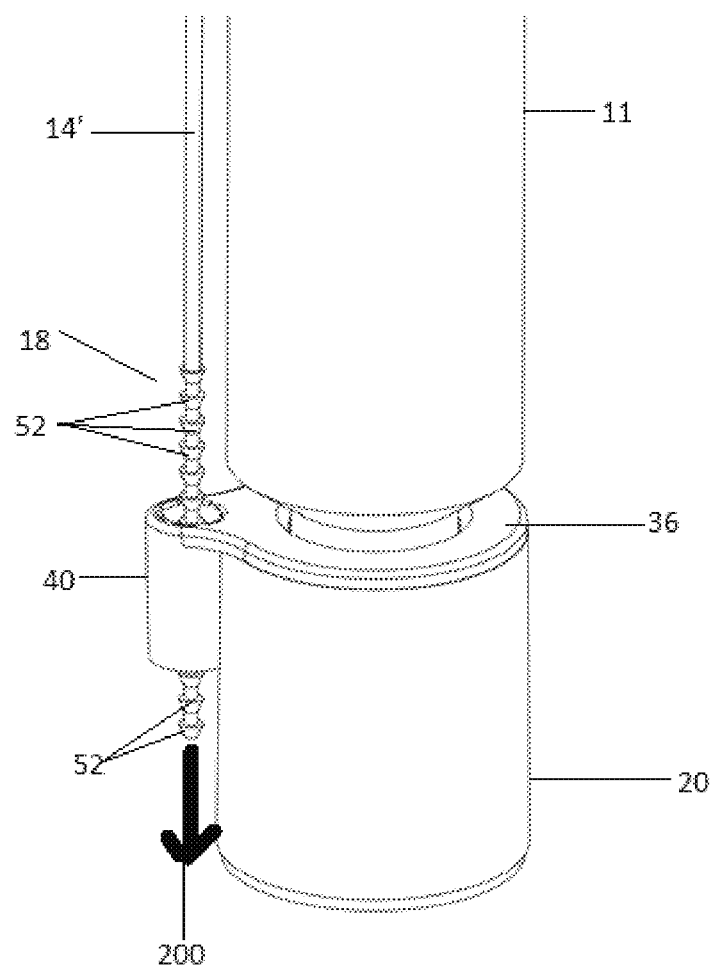
FIG. 3 is a perspective view in partial cutaway of the tamper evident assembly shown in FIG. 1.

Other structural and operative features of the tamper evident assembly 12 include the provision of a retaining segment 14', which may be defined by a length of the tether 14 that is disposed and maintained in a fixed length and taut orientation on the exterior of the syringe barrel 11, such as is partially shown in FIG. 3. As such, the retaining segment 14' is disposed between and may include, on the one hand, the proximal end 16 of the tether 14 and on the other, a connector assembly 40. As described in greater detail hereinafter, the establishment and maintenance of the retaining segment 14' in the taut, fixed length orientation is facilitated by the distal end 18 of the tether 14 only being able to move through the connector assembly 40 in a single direction, as schematically represented in FIG. 3 at 200. The taut, fixed length orientation of the retaining segment 14' is maintained by the distal end 18 of the tether 14 being connected to or maintained in a "locked" position relative to a lock member 50 of the connector assembly 40, as perhaps best shown in FIG. 4. Such a locked position of the distal end 18 of the tether 14 is maintained once the aforementioned taut, fixed length, orientation of the retaining segment 14' has been established. Therefore, the retaining segment 14' is defined and maintained by the cooperative structuring of the distal end 18 of the tether 14 and the connector assembly 40 to define a length adjusting, one-way movement of said distal end 18 through or in movable engagement with the lock member 50 of the connector assembly 40.

For purposes of clarity the term "taut" is used in describing the retaining segment 14' of the tether 14 as having and maintaining a fixed length between the proximal end 16 thereof and the connector assembly 40, associated with cover 20, due to the fact that the tether 14 may be formed of a flexible material. It may be appreciated that as a result, any slack in the retaining segment 14' is removed, as if not, it could possibly defeat the intended fixed length orientation thereof.

Therefore, when the retaining segment 14' is so oriented into the taut, fixed length orientation, both the proximal end 16 of the tether 14 and the cover 20 will be fixedly interconnected to one another and also, be respectively connected in fixed relation to the open end 11" of the barrel 11 and to the fitting 28 and/or discharge port 30 of the syringe 12. Therefore, access to the drug, medicine or other contents within the barrel interior 11', through the open end 11", is prevented or restricted by the proximal end 16 restricting removal of the plunger 13, and in particular, the stopper or piston 15 from the interior 11'. In cooperation therewith, the contents of the barrel 11 will be prevented from being removed through the discharge port 30 of the syringe 12 due to the positioning of the cover 20, which may itself be in the form of a tamper evident closure, being connected to the fitting 28. Any attempted unauthorized access to the interior 11' of the barrel 11 by a removal, breakage, alteration, etc. of the tether 14, cover 20 and/or connector assembly 40 will result in a clear indication of tampering or use.

As represented in FIGS. 7 and 7A, the proximal end 16 of the tether is illustrated in removal preventing relation to the piston or stopper 15 of the plunger 13 of syringe 10. In such a position, the proximal end 16, including the hook like structure or other depending member 16' is disposed in an interruptive, abutting engagement of the proximal end 16 with the piston 15, as the piston 15 approaches the open end 11". Due to the aforementioned fixed interconnection of the tether 14 at its proximal end 16 on the one hand, and on the other, the cover 20, via the connector assembly 40, establishment and maintenance of the taut, fixed length orientation of the retaining segment 14', will be accomplished. Once accomplished, neither the proximal end 16 of the tether 14 nor the cover 20 will be removable from their intended positions, represented throughout FIGS. 1, 3, 5 and others, without providing evidence or an indication of tampering. By way of example, if an excessive, outwardly directed force as schematically represented in FIG. 7-A by the arrow 100 is applied to the plunger 13, the tether 14 will break, and thereby provide a direct indication of tampering with the syringe 10 and its contents.

Figure 5:
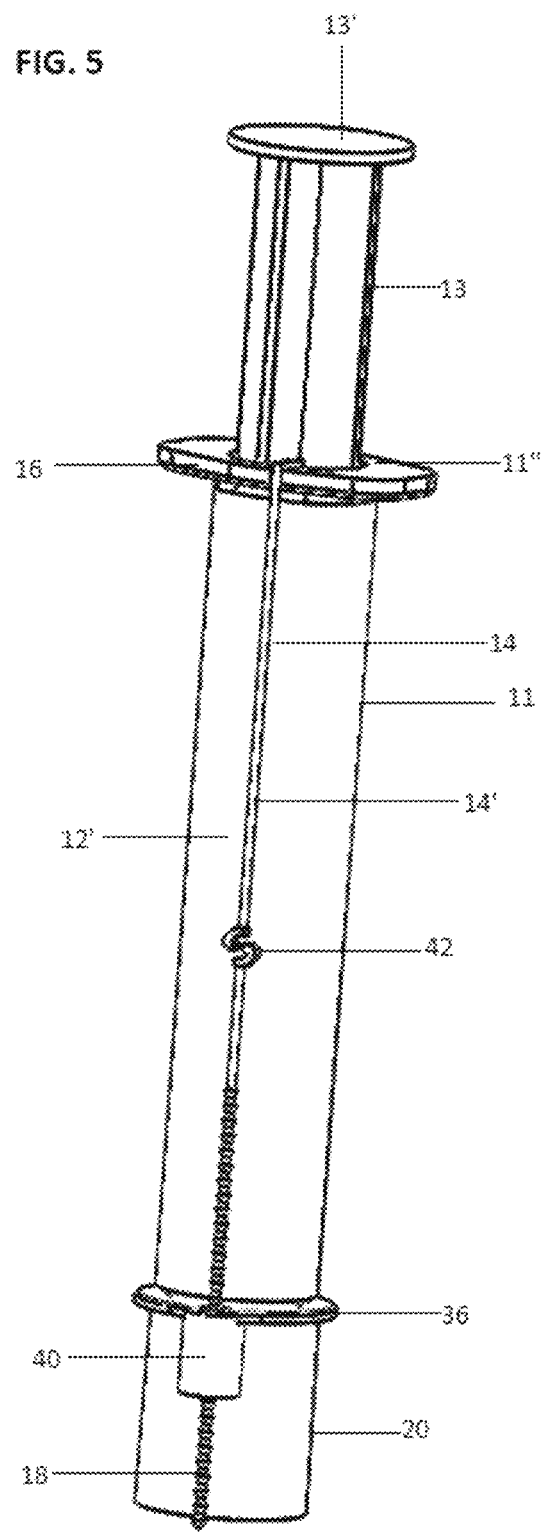
FIG. 5 is a perspective view of yet another embodiment of the tamper evident assembly of the present invention in an operative position on a syringe.
Figure 6:
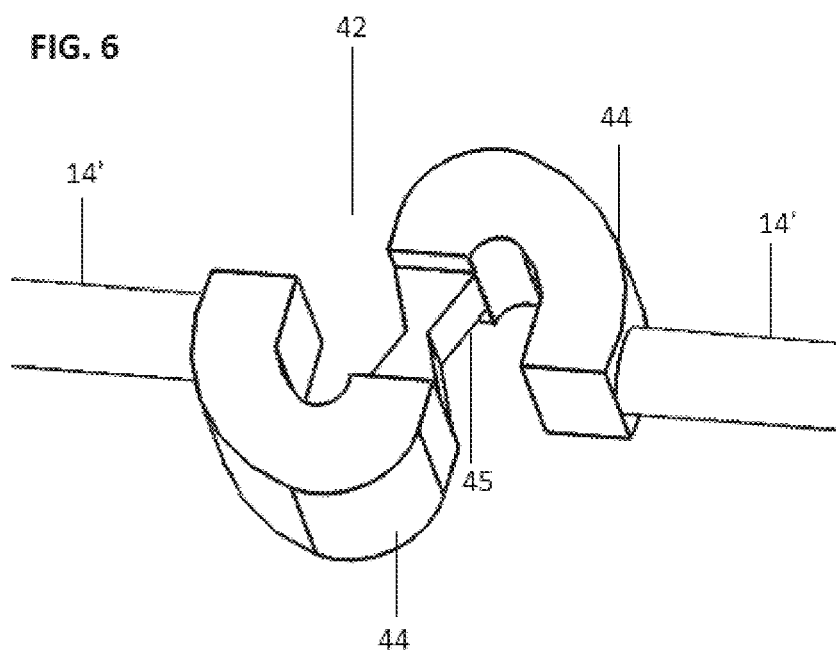
FIG. 6 is a detailed perspective view in partial cutaway of a frangible member of the elongate tether of the embodiment of tamper evident assembly shown in FIG. 5.

While a breakage along the length of the tether 14 and/or the in the retaining segment 14' provides a direct indication of tampering, the tether 14 can be formed to be even more "sensitive" to an excessive force such as shown by the arrow 100 in FIG. 7A being exerted thereon. With reference now to the additional illustrated embodiment of FIGS. 5, 6, 7 and 7A, the tether 14 may include at least one frangible link, generally indicated as 42. The frangible link 42 may have connecting portions 44 integrally or otherwise secured to corresponding portions of the retaining segment 14'. In turn, the connecting portions 44 may be removably attached to one another by a frangible segment 45 as best shown in FIG. 6. As indicated, the provision of the at least one frangible link 42 enhances the "sensitivity" of the tether 14 to an outwardly directed force 100 being exerted on the plunger 13, such as, but not limited to, when an attempt is made to remove the plunger 13 of the syringe including the stopper or piston 15 through the open end 11" of the syringe barrel 11. Therefore, the presence of the initially intact frangible link 42 makes it more difficult to manipulate the plunger 13 or tether 14 in order to remove the plunger 13 and piston 15, without breaking the at least one frangible link 42.

Still referring to FIGS. 7 and 7A, the tamper evident assembly illustrated in an alternative embodiment which incorporates the at least one frangible link 42 is shown in a completely assembled, operative position. When in this operative position, the proximal end 16 of the tether 14 is disposed in overlying relation to the perimeter of the open end 11" of the hollow interior chamber 11' of the syringe barrel 11. Concurrently, the hook like structure or depending member 16' associated with the proximal end 16 of tether 14 is at least partially disposed within the interior 11' of the syringe barrel 11, adjacent or contiguous to the open end 11". Accordingly, while the stopper or piston 15 of the syringe plunger 13 remains within the hollow interior chamber 11' in spaced relation to the open end 11", the hook like structure or depending member 16' of the proximal end will not engage or abut against the stopper or piston 15. As a result, the frangible link 42 will remain intact. However, when an outwardly directed force shown by the arrow 100 in FIG. 7A is exerted on the syringe plunger 13, it will cause the stopper or piston 15 to approach the open end 11" of the hollow interior chamber 11' in the syringe barrel 11. In turn, the hook like structure or depending member 16' will begin to contact or otherwise be disposed in an interruptive, abutting engagement with the stopper or piston 15. Continued movement of the plunger 13 and piston 15 towards or out through the open end 11" will result in a breakage of the tether, and specifically, at the at least one frangible link 42, including the frangible segment 45.

Additional structural and operative features of the connector assembly 40, which is operatively associated with the tamper evident assembly 12 and 12', include the connector assembly 40 being secured to or mounted on the cover 20. This preferred disposition of the connector assembly 40 assures that the aforementioned fixed interconnection between the cover 20 and the proximal end 16 of the tether 14, when the retaining segment 14' is in the taut, fixed length orientation, as set forth previously above. As represented in at least FIGS. 1, 3-5 and 7-7A, the tether 14 and specifically, the distal end 18 is cooperatively structured with the connector assembly 40 so as to be adjustably and movably connected to the connector assembly 40. As also indicated herein, the distal end 18 of the tether 14 and the connector assembly 40 are cooperatively structured to define a length adjusting, one-way movement of the tether 14 and the retaining segment 14' thereof. In turn, the aforementioned fixed interconnection between the proximal end 16 of the tether 14 and the cover 20 will be established and maintained, when the tamper evident assembly 12 or 12' is in the fully assembled, operative position of at least FIGS. 1 and 5.

The connector assembly 40 preferably comprises a ratchet assembly, which may be in the form of a ratchet type of connector and includes a lock member 50. In cooperation therewith, and as perhaps best illustrated in FIG. 3, the distal end 18 of the tether 14 includes a plurality of teeth 52 extending along at least a portion of the length thereof. The plurality of teeth 52 are disposed in spaced relation to one another and are dimensioned and configured to interact with the lock member 50 to facilitate the length adjusting, one-way movement of said tether 14 and distal end 18, relative to the connector assembly 40. In more specific terms, and as also represented in some of the Figures, each or at least a majority of the plurality of teeth 52 are preferably structured to include a substantially cone shape configuration. This shape of the plurality of teeth 52 facilitates the one-way movement or travel of the distal end 16 of tether 14 and plurality of teeth 52, as schematically represented by directional arrow 200 in FIG. 3. In contrast, movement or withdrawal of the distal end 18 in the opposite direction will be prevented due to the aforementioned cone shape configuration of the plurality of teeth 52.

In cooperation therewith, and as shown in FIG. 4, the lock member 50 includes a skirt or finger-like structure 50' which is at least partially flexible. Such flexibility allows the plurality of teeth 52 to pass through the skirt 50' in the intended one way direction 200 shown in FIG. 3. However, the skirt or like member 50' is biased inwardly so as to prevent movement of the distal end of the tether 14 in a direction opposite to that of direction 200, by interruptive engagement with the cone shape teeth 52.

Still referring to FIG. 4, other additional structural features include the lock member 50 being disposed at and/or within the leading or upper end of an elongated tube or sleeve structure 60. This location, as well as the length of the sleeve 60 will prevent or at least restrict access to any type of tool, such as a paperclip, screw-driver or other instrument, and prevent it from being used to reach the flexible material skirt and/or finger structure 50', in an attempt to defeat the intended operative features of the connector assembly 40.

With reference now to FIGS. 8 and 9, the installation or attachment of a syringe 11 to a cover 20, in the form of a tamper evident closure, is schematically represented. Due to the fact it is that the cover 20 is connected by way of direct contact with the fitting 28 and/or discharge port 30 of the syringe 11, it is preferably maintained in a sterile environment immediately prior to attachment to the syringe 11. Accordingly, a packaging or container generally indicated as 70 is dimensioned and configured to include at least one, but preferably, a plurality of such covers 20, wherein the connector assembly 40 may be integrally or fixedly attached to one of such covers 20. The sterility of the packaging or container 70 can be accomplished and maintained in a manner as disclosed in U.S. Pat. No. 9,311,592, which is assigned to and to be owned by a common corporate entity as is the present application.

As represented FIG. 8, attachment of the cover 20 is accomplished by first connecting the tether 14, such that the proximal end 16 of tether 14 extends into the open end 11" of the hollow interior 11' of the syringe barrel 11. The opposite or distal end 18 of the tether 14 may remain initially disconnected from the cover 20 being attached to the syringe 11. Installation proceeds by inserting the fitting 28 and nozzle or port 30 of the syringe 10 into the interior of the selected cover and rotating the syringe barrel 11 so as to accomplish a threaded engagement therewith. In order 20 to accomplish such threaded engagement, the closed end 22 of each of the covers 20, as represented in FIGS. 2 and 4, includes a similar cooperative structure to the bottom interior of the initially sterile container 70. Such cooperative structuring is also disclosed in the above noted U.S. Pat. No. 9,311,592. Once the threaded connection has been accomplished between the fitting 28 and the selected cover 20, the connected syringe 10 and cover 20 may be removed from the interior of the container 70. Thereafter, the distal end 18 of the tether 14 is pulled through the ratchet type connector assembly 40 to accomplish the taut, fixed length orientation of the retaining segment 14'. The positioning of the tamper evident assembly 12 and/or 12' in the completed, assembled operative position on the syringe 10, as respectfully represented in FIG. 1 and FIG. 5, is thereby accomplished.

Figure 10:
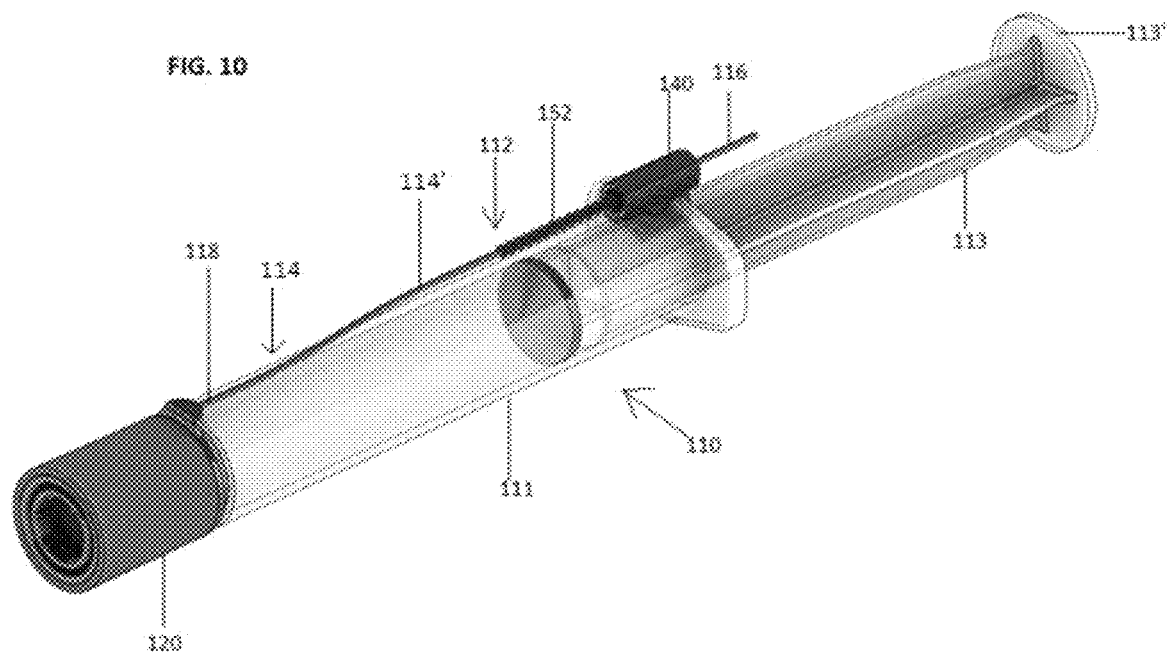
FIG. 10 is a perspective view of another embodiment of the tamper evident assembly of the present invention connected in an assembled, operative position to a syringe.
Figure 12:
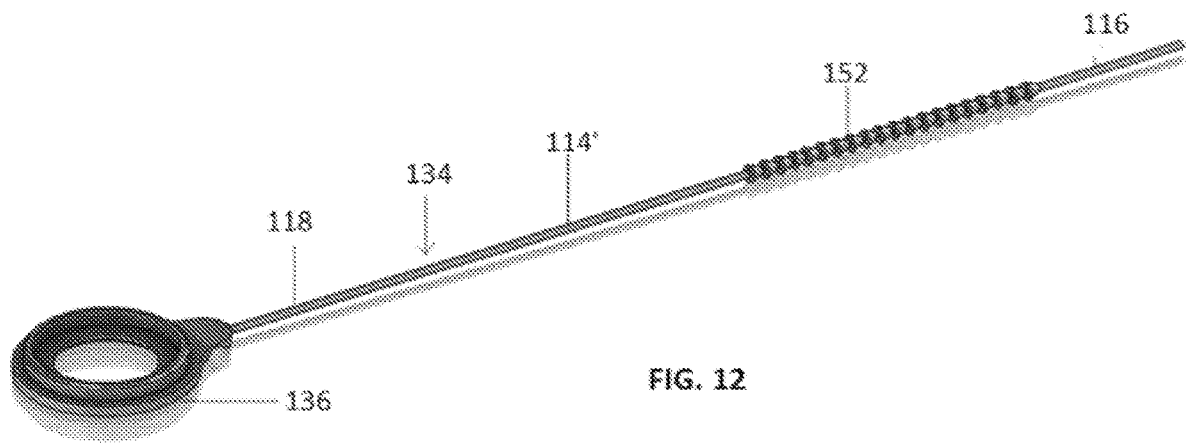
FIG. 12 is a perspective detailed view of one component of the embodiment of FIGS. 10 and 11.
Figure 13:
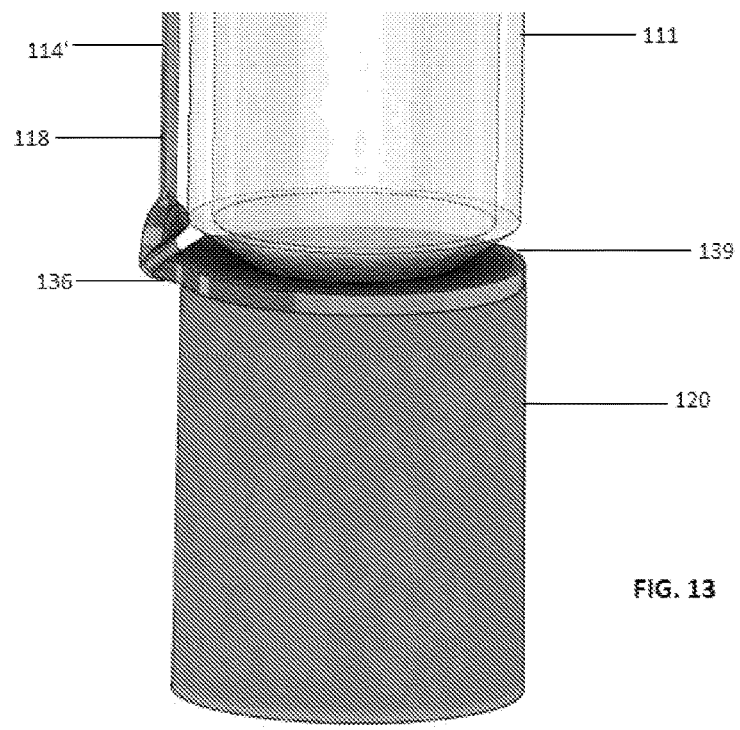
FIG. 13 is a perspective view in partial cutaway of a tamper evident closure attachable to the discharge end of the syringe as represented in FIG. 10.
Figure 14:
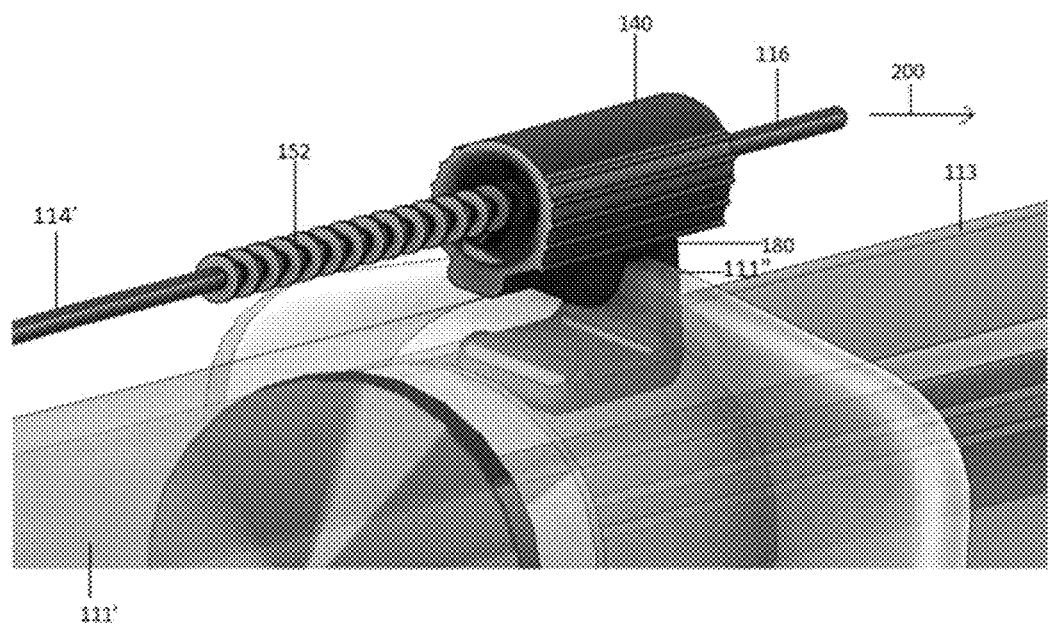
FIG. 14 is a detailed perspective view in partial cutaway of a connecting assembly attached in an operative position to both a tether component of the tamper evident assembly and to an open end of the syringe barrel.
Figure 15:
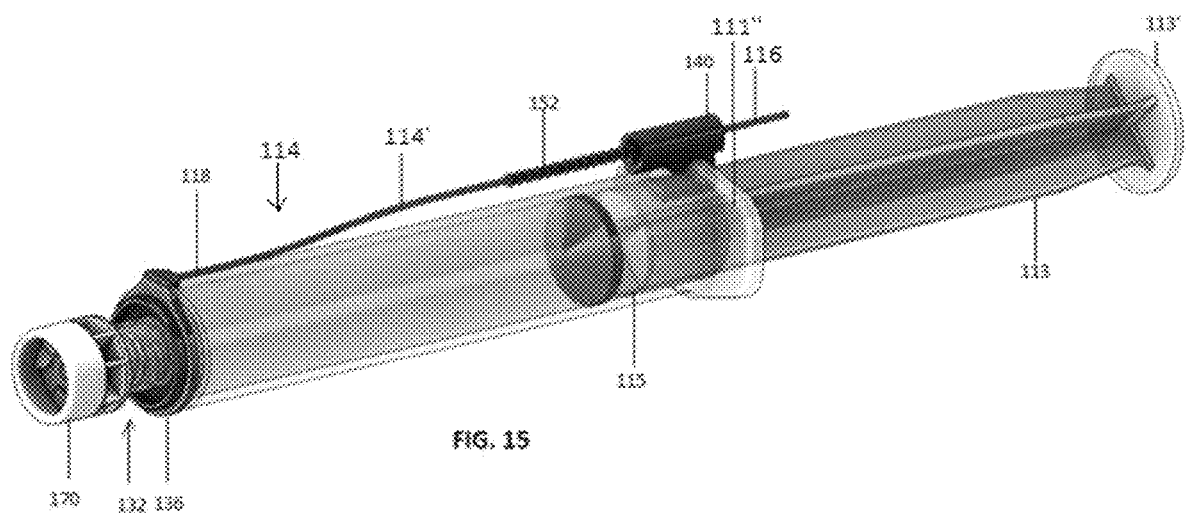
FIG. 15 is a perspective view of the embodiment of FIG. 10 attached to the syringe in a partially unassembled state and at least partially exposing the discharge end of the syringe.

Yet another embodiment of the present invention is represented in FIGS. 10-16 and includes many of the operative features of the embodiments of FIGS. 1-9, but is structurally distinguishable therefrom. This additional embodiment is directed to an assembly, also structured to have tamper evident capabilities, which prevents or restricts access to the interior of a syringe 110 such as, but not limited to, a pre-filled syringe. Therefore, the tamper evident assembly 112 is represented in FIG. 10 in an assembled state and operatively attached relation to the syringe 110, on the exterior of the barrel 111. Further, when operatively attached and positioned, the tamper evident assembly 112 is disposed on the exterior of the barrel 111, which has a hollow interior 111' (shown in FIGS. 14 and 16) in which a prescribed medicine or other contents may be stored or prefilled. Also, the barrel 111 includes an open end 111" as shown in FIG. 14, through which a plunger 113 typically enters the interior 111' of the barrel 111. As best shown in FIG. 15, the plunger 113 also includes a terminal end 113' at one end and a piston or stopper 115 connected to the opposite end thereof.

Figure 11:
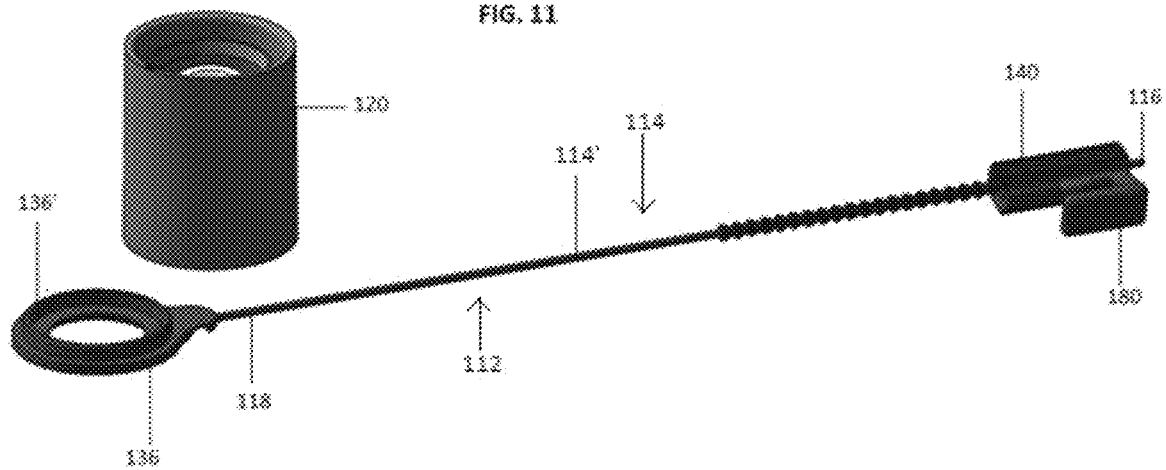
FIG. 11 is a perspective view of the various operative components of the embodiment represented in FIG. 10 in a non-attached relation to a syringe.

With reference to FIG. 11, the tamper evident assembly 112 is represented in an unassembled state and includes an elongated tether 114 having a distal end 116 and a proximal end 118. Further, the tamper evident assembly 112 may be used with a closure 120. While a closure 120 with particular structure is discussed herein, it should be appreciated that a closure having a variety of different structural configurations and operative capabilities may also be utilized and may further include any one of a plurality of different tamper evident closures.

Figure 16:
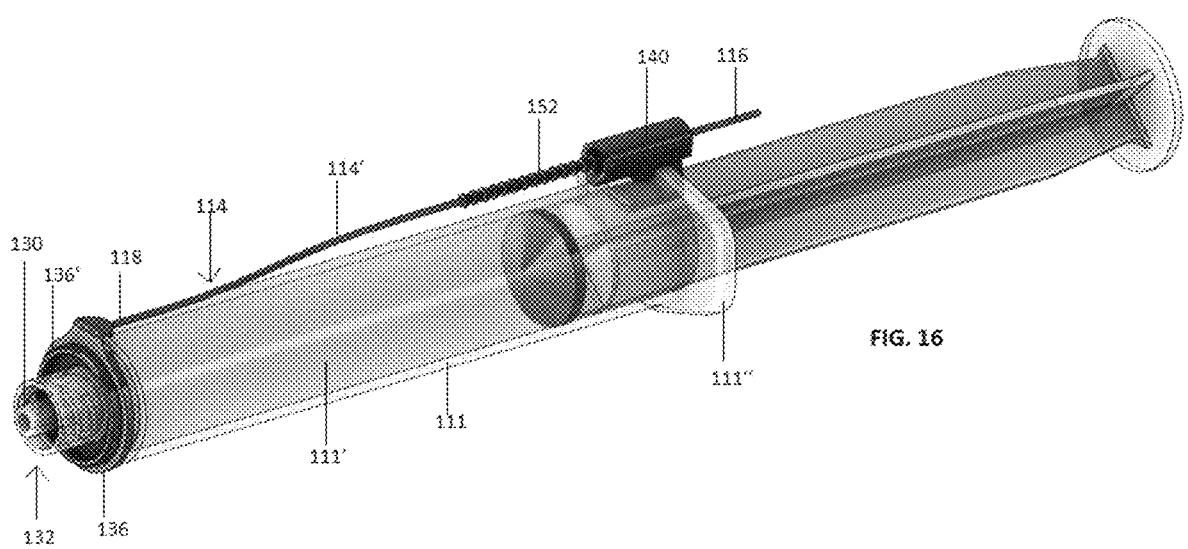
FIG. 16 is a perspective view of the embodiment of FIG. 10 attached to the syringe in a partially unassembled state and fully exposing the discharge end of the syringe.

Therefore, and by way of a non-limiting example shown in FIGS. 10, 13 and 15-16, the closure 120 is structured to engage and at least partially enclose the discharge end 132 of the syringe 110, as best shown in FIG. 15. As used herein, the discharge end 132 of the syringe 110, includes a nozzle and/or discharge port 130, which as shown in FIG. 16, is integrally or otherwise fixedly connected or associated with the discharge end 132. As set forth above, the closure 120 may be in the form of a tamper evident closure and may also include a tip cap 170, as represented in FIG. 15. The tip cap 170 is disposed in flow restricting relation to the discharge end 132 and more specifically, the syringe nozzle or discharge port 130.

One distinguishing structural feature of the embodiment of FIGS. 10-16 is that the closure 120 is not directly attached to or considered an integral part of the tamper evident assembly 112. As a result, any one of a plurality of different closures 120, may be used in combination with the tamper evident assembly 112, wherein the different closures may or may not include tamper evident capabilities independent of those associated with the tamper evident assembly 112. It should be further evident that if the closure 120 is appropriately structured, it is connected or attached to the discharge port 130 in a manner which prevents access to the contents of the interior 111' of the syringe barrel 111 through the discharge end 132 or discharge port 130.

As set forth in greater detail hereinafter, additional structural and operative features of the tamper evident assembly 112, specifically associated with the proximal end 118 of the tether, further prevent or restrict access to the prescribed medicine or other contents of the syringe barrel 111 through the discharge end 132 or discharge port 130, when the closure 120 is interconnected in covering relation thereto.

As represented throughout FIGS. 10-16, the tamper evident assembly 112 further includes a connector assembly 140 that is operatively disposed in attached relation to the barrel 111 at the open end 111" thereof. More specifically, the connector assembly 140 includes a retaining member 180, which as shown in FIGS. 11 and 14, may assume a hook-like configuration. In addition, the retaining member 180 is dimensioned and configured to extend over the outer periphery of the open end 111" and at least partially into the interior 111' of the barrel 111, as clearly represented in at least FIG. 14, when the tamper evident assembly 112 is in operative attachment to the barrel 111, as represented in at least FIG. 10. Therefore, when the aforementioned tether 114 is fixed or "locked" in a fixed length, and in a taut orientation, the position of the retaining member 180 will be maintained at least partially on the interior 111" of the syringe barrel 111, in removal restricting relation to the piston 115 of the plunger 113 associated with the syringe.

As set forth above, the tamper evident retaining assembly 112 includes the elongated tether 114. The tether 114 may be formed of an at least partially flexible and/or semi-rigid material or other materials having an increased structural integrity or rigidity. In certain instances, the tether 114 may be less than semi-rigid and more flexible, and at least initially loosely oriented until disposed in the fixed length and taut orientation, which at least partially defines the operative attachment, such as is represented in at least FIG. 10. When in the intended operative attachment, the distal end 116 is initially adjustably connected and subsequently fixedly connected to a connector assembly 140, by virtue of a lock member, similar to lock member 50 represented in FIG. 4. Although not specifically represented in FIGS. 10-16, the tamper evident assembly 112 and connector assembly 140 may incorporate the lock member 50 including a skirt or finger-like structure 50' which is at least partially flexible. Such flexibility allows a cooperatively structured distal end 116 of the tether 114 to pass through or relative to the skirt 50' in only an intended one way direction illustrated by arrow 200 shown in FIG. 3.

Accordingly, a lock member, such as lock member 50 shown in FIG. 4, is disposed on or within the connector assembly 140. A locked position and fixed connection of the distal end 116 to the connector assembly 140 is maintained, once a fixed length and taut orientation of the retaining segment 114' has been established, as represented in at least FIGS. 10 and 14-16. Therefore, the retaining segment 114' is defined by a length of the tether 114 disposed between the proximal end 118 and the distal end 116 of the tether 114, concurrent to the distal end 116 being fixedly connected to the connector assembly 140, by virtue of the lock member, when the tether 114 is disposed in the operative attachment, as at least represented in FIG. 10.

Moreover, the retaining segment 114' is disposed and maintained in the fixed length and taut orientation by the cooperative structuring of the distal end 116 of the tether 114 and the connector assembly 140 and lock member, such as lock member 50 shown in FIG. 4. As such, the distal end 116 of the tether 114 is cooperatively structured with the lock member to define the length adjusting, one-way movement of the distal end 116, such as is shown by arrow 200 in FIG. 3, through and/or relative to the lock member and connector assembly 140.

As indicated, the lock member will preferably include, similar to lock member 50 shown in FIG. 4, a skirt or finger-like structure 50' which is at least partially flexible. Such flexibility allows for a plurality of teeth 152, best shown in FIGS. 10 and 12, to pass through the skirt 50' in the intended one way direction 200 shown in FIG. 14. However, the skirt or like member 50' is biased inwardly so as to prevent movement of the distal end 118 of the tether 114 in a direction opposite to that of direction 200, by interruptive engagement with the cone shaped teeth 152.

Further, the lock member may be considered part of a ratchet assembly. As such, the ratchet assembly includes a lock member, such as lock member 50 shown in FIG. 4, which is cooperatively structured with the plurality of teeth 152 that extend along at least a portion of the length of the distal end 116 of tether 114. The plurality of teeth 152 are disposed in spaced relation to one another and are dimensioned and configured to interact with a lock member 50, as set forth above, to facilitate the length adjusting, one-way movement 200 and fixed connection of the distal end 116, relative to connector assembly 140.

As described in greater detail hereinafter, the establishment and maintenance of the retaining segment 114' in the fixed length, taut orientation is facilitated by the distal end 116 of the tether 114 only being able to move through or relative to the connector assembly 140 in a single direction, such as that shown by arrow 200 in FIG. 14. The taut, fixed length orientation of the retaining segment 114' is maintained by the distal end 116 being connected to or maintained in a "locked" position relative to the lock member, such as lock member 50 described in detail with reference to the embodiment of FIG. 4. Once the retaining segment 114' is in the locked connection with the connector 140 and retaining member 180 (best shown in FIG. 14), concurrent to the proximal end 118 of the tether being connected adjacent the discharge end 132 of the syringe as shown in FIG. 15, the retaining member 180 cannot be removed from the aforesaid "removal restricting relation" to the plunger 113 and/or piston 115 of the syringe. Therefore, removal of the retaining member 180 from its intended removal restricting relation to the piston 115 and/or plunger 113, would result in a breakage and/or removal of the tether 114, thereby providing a clear indication of tampering or use.

For purposes of clarity the term "taut" is used in describing the retaining segment 114' of the tether 114 as having and maintaining a fixed length between the proximal end 118 of the tether 114, connected adjacent and/or contiguous to the discharge end 132 and/or discharge closure 130 of the syringe, and the distal end 116 of the tether, which is fixedly connected to the connector assembly 140. Therefore, when the retaining segment 114' is so oriented into the fixed length and taut orientation, both the proximal end 118 and the distal end 116 of the tether 114 will be fixedly interconnected to one another, and also be respectively connected in fixed relation to the discharge end 132 of the syringe and open end 111" of the syringe barrel 111. Therefore, access to the contents within the barrel interior 111', through the open end 111", is prevented or restricted by the retaining member 180 being disposed at least partially within the interior 111' and in removal interruptive relation to the piston 115 and/or plunger 113. In cooperation therewith, the contents of the barrel 111 will be prevented from being removed through the discharge port 130 of the syringe 112 due to the positioning of closure 120, which itself will preferably have tamper evident capabilities, being connected in covering relation to the discharge end 132 and/or discharge port 130 of the syringe. Any attempted unauthorized access to the interior 111' of the barrel 111 by a removal, breakage, alteration, etc. of the tether 114, cover 120 and/or connector assembly 140 will result in a clear indication of tampering or use.

With reference now to FIGS. 11, 12 and 15, the proximal end 118 of the tether 114 may also be integrally connected to a collar member 136 having an outwardly extending ring 136'. The ring 136' has a central aperture enabling it to surround the exterior of the discharge end 132 of the syringe 110, and thereby, may be "fixedly" attached thereto. As used herein, the "fixed" attachment of the collar 136 in surrounding relation to the discharge end 132 is intended to describe the inability to remove the collar member 136 from the discharge end 132 without breakage or alteration of the tether 114, when in the operative attachment to the syringe barrel 111. Additional precautions for accessing the discharge end 132 of the syringe and/or "defeating" the protective structural features of the closure 120 include the provision of the collar member 136. The structure, dimension, configuration and location of the collar member 136, relative to the discharge end 132, effectively closes any spacing or open areas, such as at or near area 139 in FIG. 13, which may exist between a cover 120 and the exterior surface of the discharge end 132 and/or discharge port 130, as represented in FIG. 13. Absent the collar member 136 or other equivalent structure, an opening or space at or near 139 may be sufficiently large to allow access of a tool, instrument, etc. into the interior of the closure 120 to defeat its protective features and/or structural components.

Further, when the tether 114 is disposed in the operative attachment to the syringe barrel 111, and the retaining segment 114' is connected in locked relation to the connector assembly 140, concurrent to the collar member 136 being disposed in surrounding relation to the discharge end 132 of the syringe, the removal of the piston 115 from the interior of the barrel 111, through open end 111", is prevented or at least restricted by the locked positioning of the hook-like retaining member 180 extending at least partially through the open end 111" of the syringe barrel 111. The completed and/or assembled operative attachment of the tamper evident assembly 112 and tether 114 is thereby defined. Moreover, tamper evident protection is further facilitated by a tamper evident closure 120 being disposed in covering, enclosing and/or flow restricting relation to the discharge port 130 of the syringe 110, concurrent to the distal end 116 of the tether 114 being connected in locked relation to the connector assembly 140.

As represented in FIGS. 15 and 16, one feature of the tamper evident assembly 112 includes a collar member 136 not being fixedly connected directly to the tamper evident closure 120. As a result, the cover 120 can be independently removed from the discharge end 132 of the syringe 110, thereby exposing the tip cap 170. As a further result, a variety of different closures, which may or may not have tamper evident capabilities, may be utilized in combination with the tamper evident assembly 112. However, if tamper evident capabilities are incorporated in the closure 120, the removal thereof will also represent a direct indication of tampering or attempted use. When intended for use, the tip cap 170 is also removed from the discharge end 132, thereby allowing access to the contents of the barrel 111 through the discharge end 132 and/or discharge port 130.

Yet another feature of the present invention in the embodiment shown in FIGS. 10-16 is the ability to access the contents of the barrel 111 in an authorized and intended manner without removing the tamper evident assembly 112. This is due to the fact that the retaining member 180 is only disposed in removal restricting relation to the piston 115 through the open end 111" of the syringe barrel 111. In other words, this will not interfere with a "forward" movement of the piston 115, in the direction opposition to arrow 200 in FIG. 14, as the medicine or other contents of the barrel 111 are being discharged in the intended manner.

It is also within the spirit and scope of the present invention that the length of the tether 114 may vary so as to be used with syringes 110 of different lengths and/or sizes. As a result, the free extremity of the distal end 116 of tether 114 may extend outwardly from and beyond the connector assembly 140, but is oppositely positioned and in non-interfering relation to the discharge end 132 of the syringe 110.

In addition, the embodiment of FIGS. 10-16 may also include at least one frangible link incorporated into tether 114, such as that generally indicated as 42 in FIGS. 5, 6, 7 and 7A. As represented in the embodiment of FIGS. 1-9, the frangible link 42 may have connecting portions 44 integrally or otherwise secured to corresponding portions of the retaining segment 114'. In turn, the connecting portions 44 may be removably attached to one another by a frangible segment 45, as best shown in FIG. 6. As indicated, the provision of the at least one frangible link 42 enhances the "sensitivity"

of the tether 14 to an outwardly directed force being exerted on the plunger 113, such as, but not limited to, when an attempt is made to remove the plunger 113 of the syringe including the piston 115 through the open end 111" of the syringe barrel 111. Therefore, the presence of the initially intact frangible link 42 makes it more difficult to manipulate the plunger 113 or tether 114 in order to remove the plunger 113 and piston 115, without breaking the at least one frangible link 42.

It is also to be noted that while the closure 120 is not fixedly or integrally connected to the distal end 118 of the tether 114, there are structural and operative features associated with the tamper evident assembly 112 which allow it to be operatively associated with a container 70, as represented in FIGS. 8 and 9, as previously described above. Accordingly, a packaging or container generally indicated as 70 is dimensioned and configured to include at least one, but preferably, a plurality of such closures 120, wherein the discharge end 132 of the syringe 110 may be attached to any one of the one or more closures 120 while the tamper evident assembly 112 is disposed in operative attachment to the barrel 111. The sterility of the packaging or container 70 can be accomplished and maintained in a manner as disclosed in U.S. Pat. No. 9,311,592, which is assigned to and owned by a common corporate entity as is the present application.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A tamper evident assembly for retaining a plunger within a barrel of a syringe, said tamper evident assembly comprising:
    a tether having an elongated configuration and including a proximal end and a distal end,
    said tether structured for operative attachment to an exterior of the barrel,
    a retaining member disposable on the barrel in a removal restricting relation to the plunger,
    said operative attachment comprising said proximal end fixedly connected to the syringe in spaced relation to said retaining member,
    said operative attachment further comprising said retaining member interconnected to said distal end of the tether concurrent to disposition of said retaining member in said removal restricting relation,
    said tether comprising a retaining segment extending along at least a majority of the length thereof and disposed between said proximal end and said retaining member, concurrent to said tether being in said operative attachment,
    a connector assembly adjustably and fixedly interconnecting said distal end to said retaining member,
    said proximal end connected to the barrel adjacent a discharge port thereof; said retaining segment disposed in a fixed length, taut orientation along the barrel, between said proximal end and said retaining member, concurrent to said operative attachment of said tether, and
    said removal restricting relation comprising said retaining member at least partially disposed within an interior of the barrel in removal interruptive relation to the plunger.

2. The tamper evident assembly as recited in claim 1 wherein said retaining segment extends along a length of the barrel between said proximal end, adjacent the discharge port, and said retaining member, adjacent an open end of the barrel.

3. The tamper evident assembly as recited in claim 2 wherein said distal end is adjustably interconnected to said retaining member to define an adjustable, initially variable length of said retaining segment.

4. A tamper evident assembly for retaining a plunger within a barrel of a syringe, said tamper evident assembly comprising:
    a tether having an elongated configuration and including a proximal end and a distal end; said tether structured for operative attachment to an exterior of the barrel,
    said operative attachment comprising said proximal end fixedly connected to the barrel adjacent a discharge port thereof and said distal end disposed adjacent an open end of the barrel opposite to the discharge port,
    a connector assembly including a retaining member disposable on the barrel in a removal restricting relation to the plunger,
    said connector assembly defining an initially adjustable and subsequently fixed attachment between said distal end and the open end of the barrel, when in said operative attachment,
    said tether including a retaining segment extending along a length of the barrel between said proximal end and said connector assembly;
    said operative attachment further comprising said retaining segment disposed in a fixed length, taut orientation concurrent to said fixed attachment of said distal end to said connector assembly, and
    said removal restricting relation comprising said retaining member at least partially disposed within an interior of the barrel in removal interruptive relation to the plunger.

5. The tamper evident assembly as recited in claim 4 further comprising a collar connected to said proximal end and disposed in surrounding at least partially covering relation to an exterior of the discharge port.

6. The tamper evident assembly as recited in claim 4 wherein said connector assembly comprises a lock member cooperatively structured with said distal end to define said initially adjustable and subsequently fixed attachment therebetween; said fixed attachment defining maintenance of said retaining segment in said fixed length, taut orientation.

7. The tamper evident assembly as recited in claim 6 further including a ratchet assembly comprising said lock member and a plurality of teeth formed on said distal end; said ratchet assembly structured to define adjustable movement of said distal end relative to said lock member in a single direction.

8. A tamper evident assembly for retaining a plunger within a barrel of a syringe, said tamper evident assembly comprising:
    a tether having an elongated configuration and including a proximal end and a distal end,
    said tether structured for operative attachment to an exterior of the barrel,
    a retaining member disposable on the barrel in a removal restricting relation to the plunger,
    said operative attachment comprising said proximal end fixedly connected to the syringe in spaced relation to said retaining member,
    said operative attachment further comprising said retaining member interconnected to said distal end of the tether concurrent to disposition of said retaining member in said removal restricting relation, and said removal restricting relation comprising said retaining member at least partially disposed within an interior of the barrel in removal interruptive relation to the plunger.

9. The tamper evident assembly as recited in claim 8 further comprising a retaining segment formed on said tether between said proximal end and said retaining member, said distal end adjustably interconnected to said retaining member to define an adjustable, initially variable length of said retaining segment, between said proximal end and said retaining member.

10. The tamper evident assembly as recited in claim 8 wherein said tether comprises a retaining segment extending along at least a majority of the length of said tether between said proximal end and said retaining member, concurrent to said tether being in said operative attachment; said distal end adjustably interconnected to said retaining member to define an adjustable, initially variable length of said retaining segment.

11. The tamper evident assembly as recited in claim 10 further comprising a connector assembly disposed in adjustably and fixedly interconnecting relation between said retaining member and said distal end.

12. The tamper evident assembly as recited in claim 11 wherein said operative attachment further comprises said retaining segment disposed into a fixed length, taut orientation concurrent to said distal end fixedly interconnected to said retaining member via said connector assembly.

13. The tamper evident assembly as recited in claim 11 wherein said connector assembly comprises a lock member cooperatively structured with said distal end to define an initially adjustable and subsequently fixed attachment therebetween.

14. The tamper evident assembly as recited in claim 13 further including a ratchet assembly comprising said lock member and a plurality of teeth formed on said distal end; said ratchet assembly structured to define adjustable movement of said distal end relative to said lock member in a single direction.

15. The tamper evident assembly as recited in claim 8 further comprising a collar member fixedly connected to said proximal end in surrounding relation to a discharge port of the syringe.

16. The tamper evident assembly as recited in claim 15 wherein said collar member is disposed in at least partially covering relation to a spacing between an exterior of the discharge port and a closure interconnected to said discharge port.

17. A tamper evident assembly for retaining a plunger within a barrel of a syringe, said tamper evident assembly comprising:

a tether having an elongated configuration and including a proximal end and a distal end; said tether structured for operative attachment to an exterior of the barrel, said operative attachment comprising said distal end disposed adjacent an open end of the barrel and said proximal end fixedly connected to an end the barrel opposite to the open end, a connector assembly including a retaining member, said retaining member disposed on the barrel in a removal restricting relation to the plunger, said connector assembly defining an initially adjustable and subsequently fixed attachment of said distal end, relative to the open end of the barrel, said tether including a retaining segment extending along a length of the barrel between said proximal end and said retaining member;

said distal end adjustably interconnected to said retaining member to define an adjustable, initially variable length of said retaining segment, between said proximal end and said retaining member, and said operative attachment further comprising said retaining segment disposed in a fixed length, taut orientation concurrent to said fixed attachment of said distal end to said connector assembly.

18. The tamper evident assembly as recited in claim 17 wherein said removal restricting relation comprises said retaining member at least partially disposed within an interior of the barrel in removal interruptive relation to the plunger.

* * * * *